(12) United States Patent
Matthijs et al.

(10) Patent No.: US 7,182,987 B2
(45) Date of Patent: Feb. 27, 2007

(54) PROCESS OF INJECTION MOULDING A SYRINGE FROM POLYETHYLENE WAX CONTAINING POLYPROPYLENNE, SYRINGE OBTAINED THEREBY AND PARTICULATE COMPOSITION THEREFOR

(75) Inventors: Dirk Matthijs, Knesselone (BE); Svein Jamtvedt, Stathelle (NO); Mika Härkönen, Porsgrunn (NO); Harry Øysaed, Stathelle (NO)

(73) Assignee: Borealis Technology Oy, Porvoo (FI)

( * ) Notice: Subject to any disclaimer, the term of this patent is extended or adjusted under 35 U.S.C. 154(b) by 0 days.

(21) Appl. No.: 10/344,843

(22) PCT Filed: Aug. 15, 2001

(86) PCT No.: PCT/GB01/03653

§ 371 (c)(1),
(2), (4) Date: Jul. 29, 2003

(87) PCT Pub. No.: WO02/14045

PCT Pub. Date: Feb. 21, 2002

(65) Prior Publication Data

US 2004/0030287 A1    Feb. 12, 2004

(30) Foreign Application Priority Data

Aug. 15, 2000  (GB) .................................. 0020080.8

(51) Int. Cl.
*B32B 1/08*    (2006.01)
*A61M 5/00*    (2006.01)

(52) U.S. Cl. ...................... 428/36.9; 604/187; 604/218
(58) Field of Classification Search ............. 428/36.92, 428/36.9, 35.7; 604/187, 218
See application file for complete search history.

(56) References Cited

U.S. PATENT DOCUMENTS

| | | | |
|---|---|---|---|
| 5,338,790 A | 8/1994 | Chatterjee | |
| 5,429,603 A * | 7/1995 | Morris | ........................ 604/88 |
| 5,620,425 A | 4/1997 | Welsher et al. | |
| 6,626,862 B1 * | 9/2003 | Duchon et al. | ............. 604/110 |

FOREIGN PATENT DOCUMENTS

| | | |
|---|---|---|
| EP | 0 735 089 A2 | 10/1996 |
| JP | 56155730 | 12/1981 |
| JP | 09194648 | 7/1997 |
| JP | 10139977 | 5/1998 |
| WO | WO 9413345 | 6/1994 |

OTHER PUBLICATIONS

Database WPI, Section Ch, Week 199315, Derwent Publications, London, GB; AN 1993-120434, XP002181863, Mar. 1993.

* cited by examiner

*Primary Examiner*—Alexander S. Thomas
(74) *Attorney, Agent, or Firm*—Nixon & Vanderhye

(57) ABSTRACT

The invention provides a syringe barrel formed by injection moulding of a polypropylene composition, characterised in that said polypropylene composition contains a polyethylene wax. The invention further provides a syringe having a barrel formed by injection moulding of a polypropylene composition, characterised in that said polypropylene composition contains a polyethylene wax and a polypropylene composition suitable for such moulding.

11 Claims, No Drawings

PROCESS OF INJECTION MOULDING A SYRINGE FROM POLYETHYLENE WAX CONTAINING POLYPROPYLENNE, SYRINGE OBTAINED THEREBY AND PARTICULATE COMPOSITION THEREFOR

This invention relates to improvements in and relating to the production of injection moulded polyolefin articles, in particular polypropylene articles, more especially syringes.

Syringes are frequently produced by injection moulding of polymers. The polymers used must provide a sufficiently low friction between the outer surface of the plunger and the inner surface of the syringe barrel. In the case of polypropylene, this low friction is conventionally achieved by including a slip agent (e.g. oleamide or erucamide) in the polymer composition used for injection moulding.

However the oleamide slip agent migrates towards the surface over a period of a few weeks and causes blooming, the formation of a hazy layer which decreases the transparency of the syringe.

We have now found that by including a polyethylene wax in the polypropylene, the slip agent can be used at concentrations at which the problem of blooming is reduced or eliminated.

Thus viewed from one aspect the invention provides a syringe barrel formed by injection moulding of a polypropylene composition, characterised in that said polypropylene composition contains a polyethylene wax.

Viewed from a further aspect the invention provides a syringe having a barrel formed by injection moulding of a polypropylene composition, characterised in that said polypropylene composition contains a polyethylene wax.

While the plungers in the syringes of the invention may be made of various materials, in particular polyolefins, the syringes of the invention preferably comprise plungers having a barrel contacting surface of HDPE, in particular plungers formed by injection moulding of a HDPE composition, e.g. comprising HDPE having $MFR_{2.16}$ (190° C.) of 7 to 40 and density 955 to 964 kg/m$^3$. (MFR may be measured according to ISO 1133).

The polypropylene compositions used in the production of the syringe barrels preferably contain a slip agent, i.e. a surface friction reducing agent. Suitable slip agents include amides of fatty acids, e.g. amides of $C_{12}$ to $C_{24}$ saturated or unsaturated fatty acids, including such amides of bis or polyamines, e.g. ethylene diamine. Examples of such amides include oleamide, erucamide, stearamide, ethylene-bis-stearamide, and ethylene-bis-oleamide, and mixtures thereof. Typically such slip agents will constitute 0.02 to 0.4 wt %, preferably 0.05 to 0.25 wt, more preferably 0.1 to 0.20 wt % of the polypropylene compositions.

Oleamide is commercially available, for example as Crodamide OR from Croda Universal Ltd, Armoslip CP from Akzo Nobel or Atmer SA 1758 or 1759 from CIBA.

The polyethylene (PE) wax used according to the present invention will generally be a low molecular weight ethylene homo or copolymer, e.g. having a viscosity at 140° C. of up to 100,000 mPas (e.g. 100 to 100000 mPas or 10000 to 90000 mpas), preferably up to 50000 mPas, (e.g. 12000 to 45000 mPas) more preferably between 500 to 35000 mpas, e.g. 15000 to 35000 mPas or 22000 to 28000 mPas, particularly about 25000 mPas. Typically PE waxes with viscosity 25000 mPas at 140° C., e.g. produced by Ziegler catalysed polymerization, have a number average molecular weight (Mn) of 5 to 6 kD and an $MFR_{2.16}$ (190° C.) of 300–500 g/10 min. A viscosity of 100000 mPas at 140° C. corresponds to Mn about 8 kD and $MFR_{2.16}$ (190° C.) about 100. In contrast, polyethylene "plastics" typically have $MFR_{2.16}$ (190° C.) of below 80 g/10 min. corresponding to Mn of about 9 kD.

PE waxes are available commercially and can be produced for example by high pressure polymerization processes or using Ziegler catalysed polymerization. Typically Ziegler catalysis produces relatively high density non-polar PE wax, e.g. with densities of 930 to 980 kg/m$^3$. The high pressure processes typically produce non-polar PE waxes of lower densities, e.g. 910 to 950 kg/m$^3$, but can also be used to produce polar PE waxes of higher density, e.g. up to 1050 kg/m$^3$.

While any PE wax can be used according to the invention, it is preferred to use non-polar PE waxes of density 920 to 980 kg/M$^3$, especially 940 to 970 kg/m$^3$. Typically the PE wax will constitute 0.1 to 10 wt %, preferably 0.2 to 4 wt %, more preferably 0.5 to 2 wt % (e.g. 1.25 to 2 wt %) of the polypropylene compositions.

Examples of suitable commercially available PE waxes include Licowax PE 190 and Licowax PE 520, available from Clariant.

The polypropylene compositions may contain other components as desired, e.g. anti-oxidants, stabilizers, acid scavengers, clarifying agents, coloring agents, anti-UV agents, nucleating agents, antistatic agents, etc. Typically these will be present at less than 2 wt % each, more preferably less than 0.5 wt %, relative to the total composition weight. Examples of such components include Irganox 1010 and Irgafos 168 (stabilizers from Ciba Specialty Chemicals), calcium stearate and synthetic hydrotalcite (e.g. DHT-4A from Kyowa Chemical Industry)(acid scavengers), and 1,3:2,4-di(ethyl-benzylidene)sorbitol -EBDS (e.g. NC-4 from Mitsui Toatsu) and 1,3:2,4 bis (3,4-dimethylbenzylidene)sorbitol—DMDBS (e.g. Millad 3988 from Milliken Chemicals)(sorbitol clarifying agents).

The polypropylene used may be any propylene homo or copolymer suitable for injection moulding, especially clarified propylene homo and copolymers. Especially suitable are random propylene copolymers, e.g. containing up to 5% wt. comonomer, particularly 2 to 4% wt. comonomer, e.g. α-olefin comonomer, particularly ethylene. Comonomers preferably do not include but-1-ene. The polypropylene preferably has $MFR_{2.16}$ (230° C.) of 2 to 100 g/10 min, especially 10 to 50 g/10 min, more especially 15 to 30 g/10 min. Such polypropylenes are widely available commercially. The polypropylene preferably constitutes from 90 to 99.5 wt %, more preferably 97 to 99 wt % of the polypropylene composition.

Clarified polypropylenes can be produced for example by melt blending the polypropylene with clarifying or nucleating agents, for example sorbitol derivatives such as EDBS, MDBS (1,3:2,7-di(methyl-benzylidene)sorbitol), and DMDBS, phosphate salts (such as for example sodium 2,2'-methylenebis(4,6-di-tert.butylphenyl) phosphate), sodium benzoate, polyvinylcyclohexane, etc. Typically such clarifying or nucleating agents can result in haze levels immediately post injection moulding of below 60%, more preferably below 40%, in 2 mm thick injection moulded sheets.

The polypropylene compositions as described above form a further aspect of the invention.

Viewed from a further aspect the invention provides a process for the production of a syringe barrel comprising forming said barrel by injection moulding of a PE wax-containing polypropylene composition.

Viewed from a still further aspect the invention provides a particulate polypropylene injection moulding composition, said composition containing a PE wax and preferably also a slip agent.

The syringes according to the invention will typically have volumes, i.e. maximum injectable contents, of 0.1 to 300 mL, preferably 0.2 to 150 mL. The syringe shape may be any shape achievable by injection moulding and may be sold empty or pre-filled, e.g. with injectable liquids such as pharmaceuticals or contrast agents.

The syringe barrels of the invention will generally be cylindrical with an opening at one end for introduction of the plunger and with an opening or an openable vent at the other end through which the syringe contents may be expelled.

Injection moulding may be effected using equipment and conditions conventional for injection moulding of polypropylene.

The invention also extends to other transparent injection moulded polypropylene articles having friction surfaces, i.e., surfaces over which in use a further polymer article is intended to slide.

The invention will now be described further with reference to the following Examples.

EXAMPLE 1

| Injection Moulding Composition | |
|---|---|
| Polypropylene powder* | 100 parts by weight |
| Oleamide (Crodamide OR) | 0.15 parts by weight |
| PE-wax (Licowax PE190 from Clariant) | 1.00 parts by weight |
| Irganox B215FF (Ciba) | 0.15 parts by weight |
| DMDBS | 0.2 parts by weight |
| Synthetic hydrotalcite | 0.05 parts by weight |

*random propylene ethylene copolymer containing 3% wt. ethylene

EXAMPLE 2

Injection Moulding

Syringe barrels and plungers for a 50 mL syringe were formed by injection moulding of the composition of Example 1 and of an HDPE respectively.

EXAMPLE 3

Coefficient of Friction (COF), Haze and Visual Appearance of Injection Moulded Articles 2 mm thick polypropylene sheets were prepared by injection moulding a polypropylene composition according to the invention (substantially the same as the composition of Example 1) and a comparison composition containing no PE-wax and higher oleamide levels. The dynamic and static coefficients of friction for the sheets were determined and are set out in Table 1 below.

TABLE 1

| Composition | Oleamide % wt. | PE-wax % wt. | Static COF | Dynamic COF |
|---|---|---|---|---|
| Invention | 0.15 | 1.0 | 0.57 | 0.34 |
| Comparison | 0.25 | 0.0 | 0.60 | 0.34 |

As can be seen, the friction characteristics were substantially equivalent.

Such 2 mm thick polypropylene sheets were annealed for 72 hours at 55° C. to imitate normal "ageing" and the haze and visual appearance determined are set out in Table 2 below.

TABLE 2

| Composition | Haze | Visual Appearance |
|---|---|---|
| Invention | 42% | bare visible surface layer |
| Comparison | 51% | clearly visible greasy surface layer |

The invention claimed is:

1. A syringe barrel formed by injection moulding of a polypropylene composition, wherein said polypropylene composition contains a polyethylene wax having a viscosity at 140° C. of 500 to 35000 mPas wherein said polyethylene wax is a non-polar wax of density 920 to 980 Kg/m$^3$.

2. The barrel as claimed in claim 1 wherein said composition contains 0.1 to 10% weight of said polyethylene wax.

3. The barrel as claimed in claim 1 wherein said composition further contains a slip agent.

4. The barrel as claimed in claim 3 wherein said composition contains 0.02 to 0.5% weight of said slip agent.

5. The barrel as claimed in claim 1 wherein said composition contains a clarified polypropylene.

6. A process for the production of a syringe barrel comprising forming said barrel by injection moulding of the polypropylene composition as defined in claim 1.

7. A syringe having a barrel formed by injection moulding of a polypropylene composition, wherein said polypropylene composition is as defined in claim 1.

8. The syringe as claimed in claim 7 having a polyolefin plunger.

9. The syringe as claimed in claim 8 having an HDPE plunger.

10. The syringe as claimed in claim 7 containing an injectable liquid.

11. The barrel as claimed in claim 1 wherein said polyethylene wax has a viscosity at 140° C. of 15,000 to 35,000 mPas.

* * * * *